US00PP12948P2

(12) United States Plant Patent
Vandenberg

(10) Patent No.: US PP12,948 P2
(45) Date of Patent: Sep. 10, 2002

(54) CHRYSANTHEMUM PLANT NAMED 'YOSWIFT'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 66 days.

(21) Appl. No.: 09/748,693

(22) Filed: Dec. 27, 2000

(51) Int. Cl.[7] ..... A01H 5/00

(52) U.S. Cl. ..... Plt./286

(58) Field of Search ..... Plt./286, 287, 294, Plt./297, 288

(56) References Cited

PUBLICATIONS

UPOV–ROM, 2001/04, Plant Variety Database, GTI Jouve Retrieval Software, citation for 'Yoswift'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yoswift', characterized by its anemone-type inflorescences that are about 5.1 cm in diameter with large anemone centers; attractive white ray and dark purple-tipped disc florets; very freely flowering habit with numerous inflorescences per stem; early flowering, response time about 50 days; dark green foliage; strong stems; and good postproduction longevity with inflorescences maintaining good substance and color for about three weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Yoswift'.

The new Chrysanthemum is a product of a planned breeding program conducted by the Inventor in Salinas, Calif. The objective of the breeding program is to create new cut Chrysanthemum cultivars having inflorescences with desirable colors and good form and substance.

The new Chrysanthemum originated from a cross made by the Inventor in June, 1994, in Salinas, Calif., of the Chrysanthemum cultivar Colon, not patented, as the male, or pollen, parent with a proprietary Chrysanthemum seedling selection identified as 0098, as the female, or seed, parent.

The cultivar Yoswift was discovered and selected by the Inventor as a flowering plant within the progeny of the stated cross in a controlled environment in Alva, Fla., in November, 1995. The selection of this plant was based on its desirable inflorescence colors and good form and substance.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Yoswift has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoswift'. These characteristics in combination distinguish 'Yoswift' as a new and distinct cultivar:

1. Anemone-type inflorescences that are about 5.1 cm in diameter and with large anemone centers.
2. Attractive white ray and dark purple-tipped disc florets.
3. Very freely flowering with numerous inflorescences per stem.
4. Early flowering, response time is about 50 days.
5. Dark green foliage.
6. Thick and strong stems.
7. Good postproduction longevity with inflorescences maintaining good substance and color for about three weeks in an interior environment.

Plants of the new Chrysanthemum can be compared to plants of the cultivar Mascota, disclosed in U.S. Plant Pat. No. 11,994. In side-by-side comparisons conducted in Salinas, Calif., plants of the new Chrysanthemum and the cultivar Mascota differed in the following characteristics:

1. Plants of the new Chrysanthemum have shorter leaves and shorter petioles than plants of the cultivar Mascota.
2. Plants of the new Chrysanthemum have more inflorescences per stem than plants of the cultivar Mascota.
3. Plants of the new Chrysanthemum have slightly smaller inflorescences but larger anemone centers than plants of the cultivar Mascota.
4. Ray florets of plants of the new Chrysanthemum are more upright than ray florets of plants of the cultivar Mascota.
5. Plants of the new Chrysanthemum have shorter peduncles than plants of the cultivar Mascota.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Yoswift' grown as a spray-type cut Chrysanthemum.

The photograph on the second sheet comprises a close-up view of typical inflorescences of 'Yoswift'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on May 30, 2000 and received 21 long day/short nights followed by short day/long nights until flowering. Plants were grown as single-stem cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Aug. 21, 2000.

Botanical classification: *Chrysanthemum×morifolium* cultivar Yoswift.

Commercial classification: Anemone spray-type cut Chrysanthemum.

Parentage:

*Male or pollen parent.*—*Chrysanthemum×morifolium* cultivar Colon, not patented.

*Female or seed parent.*—Proprietary *Chrysanthemum×morifolium* seedling selection identified as code number 0098, not patented.

Propagation:

*Type.*—Terminal tip cuttings.

*Time to rooting.*—Seven to ten days with soil temperatures of 21° C.

*Root description.*—Fine, fibrous and well-branched.

Plant description:

*Appearance.*—Herbaceous anemone spray-type cut flower.

*Flowering stem description.*—Aspect: Erect. Length: About 91.4 cm. Diameter: About 8 mm. Texture: Pubescent. Color: 144A to 146A.

*Foliage description.*—Arrangement: Alternate. Length: About 10.1 cm. Width: About 7.7 cm. Apex: Cuspidate to mucronate. Base: Mostly truncate. Margin: Palmately lobed; sinuses mostly parallel. Texture: Upper and lower surfaces pubescent. Veins prominent on lower surface. Color: Young foliage upper surface: Darker than 147A. Young foliage lower surface: Darker than 147B. Mature foliage upper surface: Darker than 147A; venation, close to 147B. Mature foliage lower surface: Close to 147B; venation, close to 146B. Petiole: Length: About 1.8 cm. Diameter: About 3 mm. Color: Close to 146B.

Flowering description:

*Appearance.*—Anemone spray-type inflorescence form with elongated oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 50 days later.

*Postproduction longevity.*—In an interior environment, flowering stems will maintain good color and substance for about three weeks in an interior environment after one week of cool storage.

*Quantity of inflorescences.*—Freely flowering with about 18 inflorescences per flowering stem.

*Inflorescence size.*—Diameter: About 5.1 cm. Depth (height): About 2.1 cm. Diameter of disc: About 3.5 cm. Diameter of receptacle: About 5.5 mm.

*Ray florets.*—Shape: Elongated oblong. Length: About 2.9 cm. Corolla tube length: About 5 mm. Width: About 7.5 mm. Corolla tube diameter: About 1 mm. Apex: Mostly acute, occasionally emarginate. Base: Attenuate. Margin: Entire. Texture: Satiny, smooth, glabrous; longitudinally ridged. Aspect: Mostly flat. Aspect: Initially upright; when mature, about 45° from vertical. Number of ray florets per inflorescence: About 26 arranged in one or two rows. Color: When opening, upper surface: White ground color, close to 155D; overlain with longitudinal faint purple, close to 71A to 77A, stripes. When opening, lower surface: White ground color, close to 155D; underlain with longitudinal faint purple, close to 77A, stripes. Mature, upper surface: White ground color, close to 155D; overlain with longitudinal faint purple, close to 77A, stripes. With subsequent development, stripes fade and florets become completely white. Mature, lower surface: White ground color, close to 155D; underlain with longitudinal faint purple, close to 77A, stripes.

*Disc florets.*—Shape: Enlarged tubular; flared. Length: About 2.1 cm. Width: Apex: About 4 mm. Base: About 1 mm. Number of disc florets per inflorescence: Numerous, typically about 154. Color: Immature: Apex: More red than 79A to close to 187A. Mid-section and base: Close to 145A. Mature, tube: Apex: More red than 79A to more intense purple than 77A. Mid-section: White, close to 155D, ground color overlain with longitudinal purple, 77A, stripes. With subsequent development, stripes fade to white. Base: 154A. Mature, throat: Mostly white, close to 155D, with faint purple, close to 77A, longitudinal stripes.

*Peduncle.*—Aspect: Strong, angled about 45 to 50° from vertical. Length: First peduncle: About 5.6 cm. Fourth peduncle: About 6.75 cm. Seventh peduncle: About 10 cm. Diameter: About 3 mm. Texture: Very fine pubescence. Color: 144A to 146A.

*Reproductive organs.*—Androecium: Present on disc florets only. Anther color: 9A. Amount of pollen: Scarce. Pollen color: 12A. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures as high as 40° C.

It is claimed:

1. A new and distinct cultivar of Chrysanthemum plant named 'Yoswift', as illustrated and described.

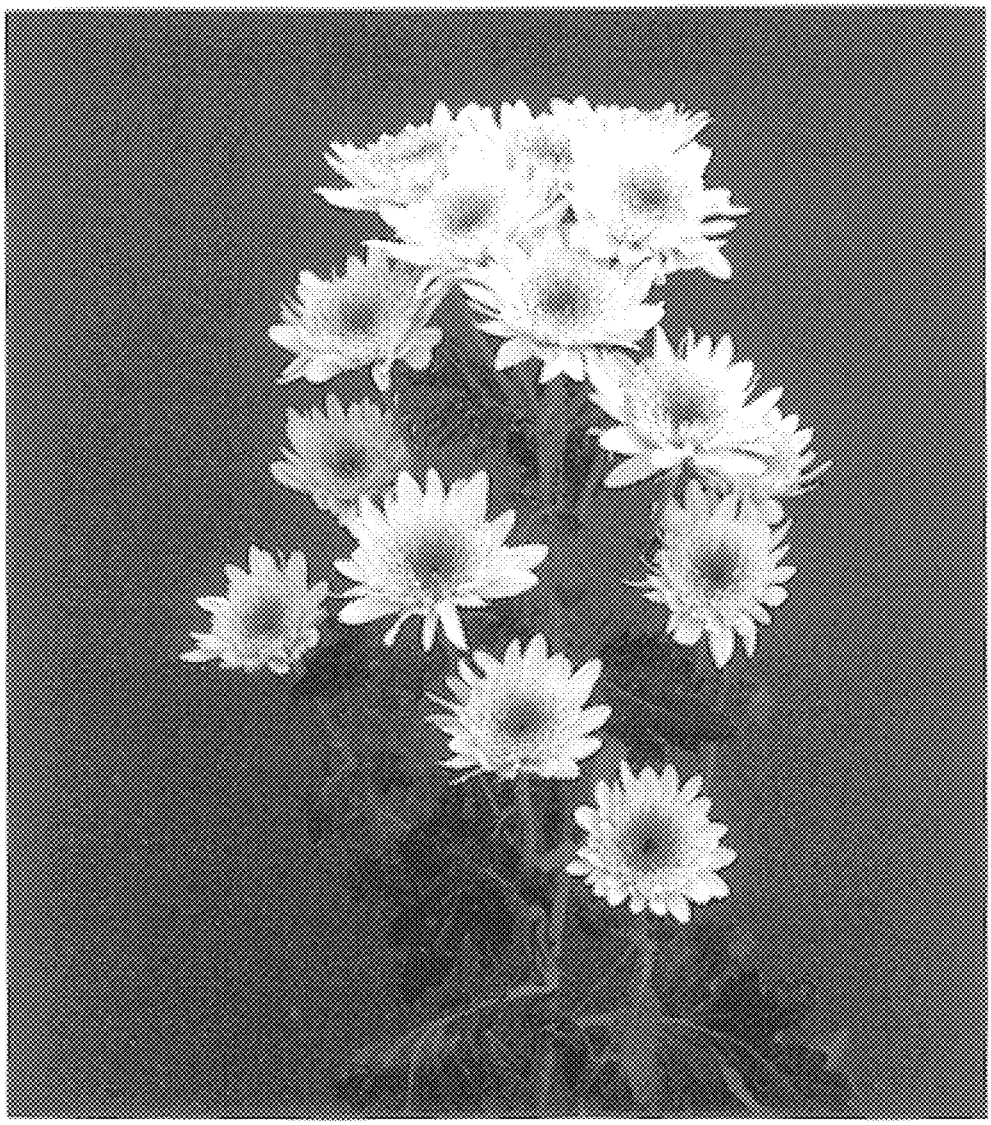

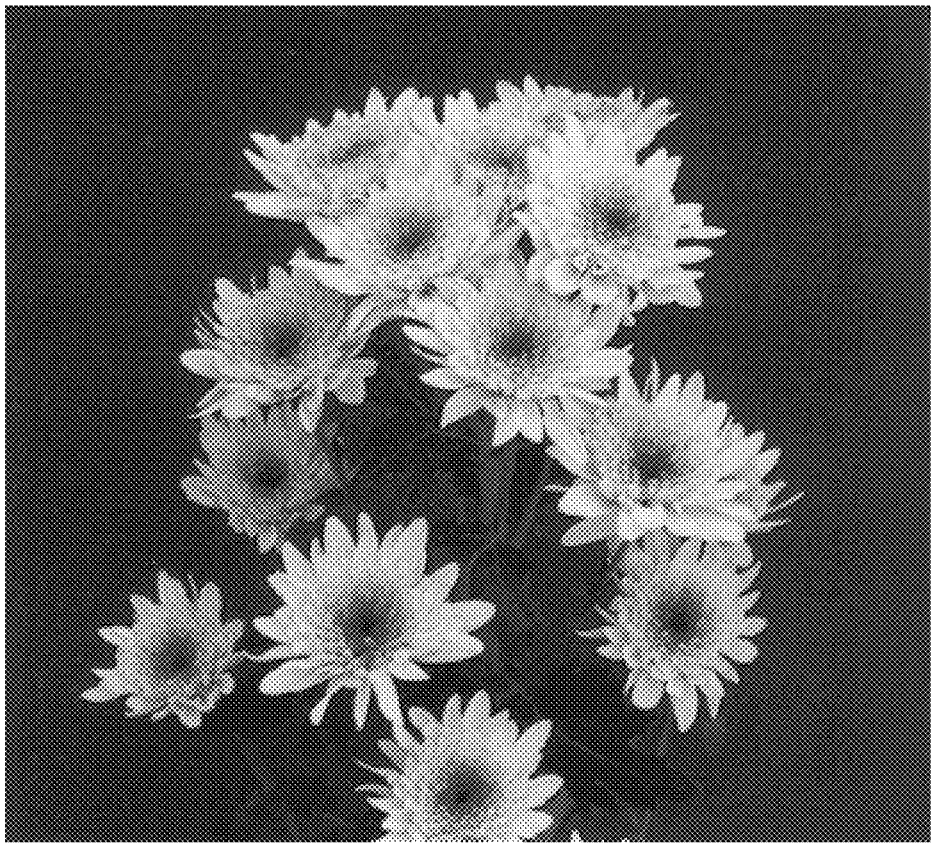

* * * * *